US012279985B2

(12) United States Patent
Romo et al.

(10) Patent No.: US 12,279,985 B2
(45) Date of Patent: Apr. 22, 2025

(54) BRACE WITH SLIDABLE, INTERNAL LATERAL PANEL

(71) Applicant: Aspen Medical Products, LLC, Irvine, CA (US)

(72) Inventors: Albert V. Romo, Lakewood, CA (US); Geoffrey Wong, Costa Mesa, CA (US)

(73) Assignee: Aspen Medical Products, LLC, Irvine, CA (US)

( * ) Notice: Subject to any disclaimer, the term of this patent is extended or adjusted under 35 U.S.C. 154(b) by 207 days.

(21) Appl. No.: 17/687,592

(22) Filed: Mar. 4, 2022

(65) Prior Publication Data

US 2022/0280326 A1 Sep. 8, 2022

Related U.S. Application Data

(60) Provisional application No. 63/157,441, filed on Mar. 5, 2021.

(51) Int. Cl.
*A61F 5/02* (2006.01)

(52) U.S. Cl.
CPC .................................. *A61F 5/028* (2013.01)

(58) Field of Classification Search
CPC .... A61F 5/028; A61F 5/02–03; A61F 5/0193; A61F 5/01; F41H 1/02
USPC ........................................................ 602/5, 19
See application file for complete search history.

(56) References Cited

U.S. PATENT DOCUMENTS 4,022,197 A * 5/1977 Castiglia ............... A61F 13/143 602/61
4,838,043 A * 6/1989 Jencks ................. D04B 21/202 66/170
5,318,505 A * 6/1994 Sou ......................... A61F 5/028 2/338
5,690,609 A 11/1997 Heinze, III
5,830,168 A * 11/1998 Finnell .................. A61F 5/0193 602/23
6,336,908 B1 1/2002 Slautterback
6,500,137 B1 * 12/2002 Molino .................. A61F 5/022 602/19

(Continued)

FOREIGN PATENT DOCUMENTS

WO 03/088877 A1 10/2003
WO 2005/117769 A1 12/2005

OTHER PUBLICATIONS

PCT/US2022/019049 filed Mar. 5, 2022 International Search Report and Written Opinion dated Jul. 5, 2022.

(Continued)

*Primary Examiner* — Keri J Nelson
*Assistant Examiner* — Seth R. Brown
(74) *Attorney, Agent, or Firm* — Rutan & Tucker, LLP

(57) ABSTRACT

A brace configured to wrap around a lumbar region of a wearer features a first arm and a second arm. Each arm features a first band, a panel slidably disposed at a lateral side of the wearer and coupled to the first band, and a loop connector coupled to the panel on a first end of the panel. The first band has a horizontally extending channel, within which the panel moves. The panel features a rigid material, and the loop connector is tethered to the panel. Moving the connector loop causes moving the panel laterally, which adjusts a location of the panel around the lumbar region of the wearer. The brace may further feature an upper band and a lower band.

20 Claims, 3 Drawing Sheets

(56) References Cited

U.S. PATENT DOCUMENTS

| | | | | |
|---|---|---|---|---|
| 12,036,142 | B1 * | 7/2024 | Fried | A61F 5/024 |
| 2002/0032397 | A1 * | 3/2002 | Coligado | A61F 5/028 602/5 |
| 2010/0152636 | A1 * | 6/2010 | Parks | A61F 5/028 602/33 |
| 2010/0168630 | A1 * | 7/2010 | Cropper | A61F 5/024 602/19 |
| 2010/0205708 | A1 * | 8/2010 | Storms, Jr. | A41D 13/05 2/2.5 |
| 2011/0105971 | A1 | 5/2011 | Ingimundarson et al. | |
| 2011/0295169 | A1 | 12/2011 | Hendricks | |
| 2013/0006158 | A1 | 1/2013 | Ingimundarson et al. | |
| 2013/0237891 | A1 | 9/2013 | Fryman et al. | |
| 2014/0058306 | A1 * | 2/2014 | Bannister | A61F 5/028 602/19 |
| 2014/0058307 | A1 | 2/2014 | Marshall | |
| 2014/0135672 | A1 | 5/2014 | Joseph et al. | |
| 2014/0228727 | A1 | 8/2014 | Burke et al. | |
| 2017/0325988 | A1 * | 11/2017 | Nadeau | A61F 5/026 |
| 2019/0343673 | A1 | 11/2019 | Wolanske et al. | |
| 2020/0060860 | A1 * | 2/2020 | Kramer | A61F 5/32 |
| 2021/0196029 | A1 * | 7/2021 | Dabrowka | F41H 1/02 |
| 2022/0226139 | A1 | 7/2022 | Poker et al. | |
| 2022/0280325 | A1 | 9/2022 | Romo et al. | |
| 2023/0181346 | A1 | 6/2023 | Romo | |

OTHER PUBLICATIONS

U.S. Appl. No. 17/687,567, filed Mar. 4, 2022, Restriction Requirement dated Jul. 6, 2023.

U.S. Appl. No. 17/687,567, filed Mar. 4, 2022, Final Office Action dated May 30, 2024.

U.S. Appl. No. 17/687,567, filed Mar. 4, 2022, Non-Final Office Action dated Aug. 28, 2024.

U.S. Appl. No. 17/687,567, filed Mar. 4, 2022, Non-Final Office Action dated Dec. 28, 2023.

EP22764207.1 filed Oct. 5, 2023, Partial European Search Report dated Dec. 12, 2024.

U.S. Appl. No. 17/687,567, filed Mar. 4, 2022, Final Office Action dated Dec. 27, 2024.

U.S. Appl. No. 18/083,358, filed Dec. 16, 2022 Non-Final Office Action dated Jan. 29, 2025.

* cited by examiner

BRACE WITH SLIDABLE, INTERNAL LATERAL PANEL

CROSS-REFERENCE TO RELATED APPLICATIONS

This application claims the benefit of priority on U.S. Provisional Patent Application No. 63/157,441 filed Mar. 5, 2021 the entire contents of which are incorporated by reference herein.

FIELD

Embodiments of the disclosure relate to the field of medical devices. More specifically, one embodiment of the disclosure relates to braces with repositionable lateral panels and components thereof.

GENERAL BACKGROUND

The following description includes information that may be useful in understanding the described invention. It is not an admission that any of the information provided herein is prior art or relevant to the presently claimed invention, or that any publication specifically or implicitly referenced is prior art.

Orthopedic lumbar braces (orthoses) usually need to be adjusted or customized in some manner to conform to the body part(s) being braced, and then properly positioned. A typical orthosis commonly has at least two portions, a rigid portion supporting a body part, and a flexible or semi-flexible portion securing the orthosis to the body. Various types of lumbar braces, such as a thoracic-lumbar-sacral orthosis (TLSO) for example, are used to provide support and stabilization of the spine normally after a back injury and/or surgery, and in some cases, may be utilized to address spinal pathologies. A TLSO is a brace that limits movement in a wearer's spine from the thoracic area (mid-back area) to the wearer's sacrum (lower-back area). At the same time, the TLSO allows a wearer's neck to move freely.

Conventional braces provide for partial or substantial immobilization of the torso, back or other portion of a wearer's body. There are thoracic lumbar sacral orthosis back brace with an adjustable sliding back panel, although fail to use any lateral panels. There is a need for an improved brace with repositionable lateral panels that provide support, comfort and ease of use to the patient.

BRIEF DESCRIPTION OF THE DRAWINGS

Embodiments of the invention are illustrated by way of example and not by way of limitation in the figures of the accompanying drawings, in which like references indicate similar elements and in which.

DETAILED DESCRIPTION

Figure 1:
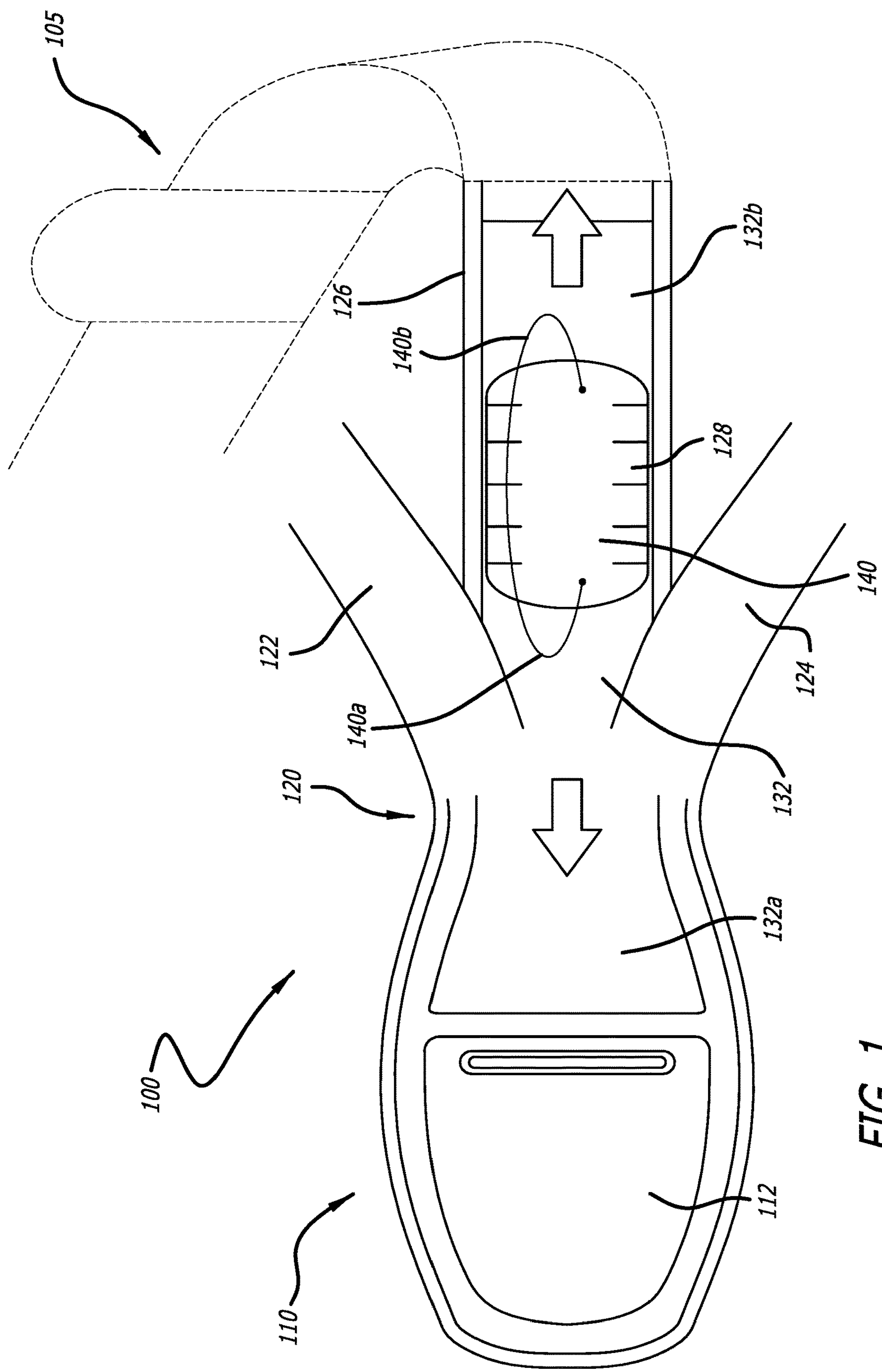
FIG. 1 is a perspective outside view of a first exemplary embodiment of a brace with slidable, internal lateral panel.

As noted above, conventional braces provide for partial or substantial immobilization of the torso, back or other portion of a wearer's body. The thoracic lumbar sacral orthosis back brace with adjustable sliding back panel fail to use any lateral panels. There is a need for an improved brace with repositionable lateral panels that provide support, comfort and ease of use to the patient. In order to tackle this issue, a brace with slidable, internal lateral panel is disclosed.

Embodiments of the present disclosure generally relate to a lumbar brace including slidable, internal lateral panels. According to a first embodiment of the disclosure, the lumbar brace is configured to wrap around a lumbar region of a wearer and features a first arm around a first side of the wearer, and a second arm around a second side of the wearer. Each arm features a first band, a panel slidably disposed at a lateral side of the wearer and coupled to the first band, and a loop connector coupled to the panel. The first band has a horizontally extending channel, within which the panel moves. Configured to provide lateral support for the wearer, the panel features a rigid material, and the loop connector is tethered to the panel.

Herein, rotational movement of the connector loop causes lateral movement of the panel, which adjusts a location of the panel around the lumbar region of the wearer. The rotational movement of the connector loop may be restricted to restrain lateral movement of the panel to a prescribed area of the first band. According to various embodiments of the present disclosure, the location of the panel is adjusted based on the size of the wearer of the brace. In general, while a first position might be desirable, e.g., comfortable, for a first wearer, the same position is undesirable, e.g., uncomfortable, for another wearer who is larger in size compared to the first wearer. As another component to provide additional comfort for the wearer, the brace may further feature an upper band and a lower band, as described in a concurrently filed U.S. Patent Application entitled "Adjustable Multi-Band Spine Bracing System," the entire contents of which are incorporated by reference herein.

In various embodiments of the present disclosure, one or more tubes, cords, or wires may be inserted into the channel. For example, wires or cords connected to medical equipment and monitors and/or tubes, e.g., catheters, can be inserted into the channel for wire/tube management.

In embodiments, moving the handle member may cause the panel to move horizontally within the channel, thus the wearer can adjust the location of the panel. In particular, based on a size of the wearer, the desired location of the panel changes. The handle member helps the wearer to easily adjust the panel and reposition the panel to a desired location.

According to a second embodiment of the disclosure, the lumbar brace is configured to wrap around a lumbar region of a wearer and features a first band, and a panel slidably disposed within a channel on the first band. A lateral movement of the panel in the channel is constrained by a first and a second boundary at a first and a second end of the channel, respectively. The lumbar brace may feature a handle member disposed on the panel. The handle member may be a tube knitted to the panel, a leash or any other suitable handle. The lumbar brace may further feature an upper and a lower band, which the first band may be disposed between an upper band and a lower band. The panel includes a rigid material, and the lateral movement of the panel adjusts a location of the panel around the lumbar region of the wearer.

According to a third embodiment of the disclosure, the lumbar brace is configured to wrap around a lumbar region of a wearer and features a first band having has a horizontally extending channel, a panel slidably disposed at a lateral side of the wearer within the channel, and a plurality of openings disposed on the first band. The panel is laterally slidable between the plurality of openings. The lumbar brace may further feature a second band and a third band disposed on upper side and lower side of the first band, respectively. The channel may extend along the entire length of the first band, and the plurality of openings may be disposed along the channel. Sliding the panel between the plurality of openings may adjust the location of the panel around the lumbar region of the wearer.

As described herein, the lumbar brace may constitute any type of lumbar sacral orthosis (LSO), including a standard LSO (lower back brace belt) or other orthoses configured to provide greater patient immobilization, such as a thoracic LSO (TLSO), or a cervical TLSO (CTLSO) as described below.

Each of the components described herein may be formed, at least in part, with a rigid material, such as hardened plastic for example, to provide greater stiffness for immobilization of the patient. Herein, the posterior portion of the lumbar brace is shaped and sized to rest against the mid-to-lower portions of the patient's back to partially immobilize the spine of the patient. When worn, the posterior portion is oriented to reside or is substantially in parallel with a back plane of the patient and provide support along a thoracic and lumbar regions of the patient's spine. A lateral portion of each arms of the lumbar brace may cover one side of the patient. An anterior portion resides or substantially is parallel with a frontal plane of the patient, and is contact with the abdominal region of the patient's spine. It is contemplated that each of the first and second arm includes a posterior portion covering the back of the wearer, a lateral portion covering the sides of the wearer, and an anterior portion covering the front of the wearer.

Each arm's anterior portion may include a coupling section to removably attach to the other anterior portion, e.g., via hook fasteners such as VELCRO® strips. Alternatively, the arms' anterior portions are removably coupled together by using a hook and loop coupling.

I. Terminology

In the following description, certain terminology is used to describe aspects of the invention. For example, the term "member" may be construed as a structural component of an orthopedic brace. In certain situations, a member may include a component covered by soft goods such as one or more textiles, one or more fabrics (woven fabrics and/or non-woven fabrics), leathers, and/or another covering material. These soft goods may feature "loop" type fasteners or other variants to which a "hook" type fastener may be attached or may feature a hook-type fastener for attachment to a loop-type fastener. In other situations, the member may be soft goods attached to another structural component of the orthopedic brace such as a textile or fabric sewn to form together such as a knit textile with pockets in which the structural component(s) can be positioned within the pocket(s).

The term "channel" is a partially-enclosed housing, namely a structure having partially enclosed perimeter except for at least one opening at an end of the channel (and perhaps two openings at the end of the channel). As a result, a partially-enclosed chamber operates as a structure that is configured to secure, maintain and protect components, such as a lateral panel or one or more tubes, wires, cables, cords or other interconnects passing there through.

The term "attach" and other tenses of the term (attached, attaching, etc.) may be construed as physically connecting a first member to a second member. A "fastener" may be construed as any physical component that is used to attach different members together. An illustrative example of different types of fasteners and fastening techniques may include, but are not limited or restricted to snaps, buttons, clasps, buckles, adhesives, sewing, heat sealing (or melting), gluing, knitting, or other physical coupling techniques such as a hook and loop connection.

The terms "rigid" or "rigidity" with respect to a member or portion of a member may be construed as the member being configured to at least partially resist bending or deformation. According to this definition, different lengths of a given structure and composition can be rigid at a shorter length, and flexible at a longer length. As used herein, the term "rigid" with respect to a member or portion of a member may be construed as the member will be permanently deformed or broken if bent or twisted by at least 90°.

Finally, the terms "or" and "and/or" as used herein are to be interpreted as inclusive or meaning any one or any combination. As an example, "A, B or C" or "A, B and/or C" mean "any of the following: A; B; C; A and B; A and C; B and C; A, B and C." An exception to this definition will occur only when a combination of elements, functions, steps or acts are in some way inherently mutually exclusive.

As this invention is susceptible to embodiments of many different forms, it is intended that the present disclosure is to be considered as an example of the principles of the invention and not intended to limit the invention to the specific embodiments shown and described.

II. General Architecture

Referring to FIG. 1, a perspective outside view of a first exemplary embodiment of an arm 100 of a brace with one or more slidable, internal lateral panels is shown. It should be noted that, the arm 100 with a slidable, internal lateral panel 128 is a portion of a brace 105 (e.g., LSO, TLSO, CTLSO, etc.) that includes two arms, each covering one side of the wearer. Each arm (e.g., arm 100) of the brace with slidable, internal lateral panel 128 includes an anterior portion 110 (i.e., a front portion), a lateral portion 120, and a posterior portion (i.e., a back portion, not shown). The posterior portion is oriented, when worn, to generally reside or is substantially in parallel with a back plane of the patient. The posterior portion may provide support along a thoracic and lumbar regions of the patient's spine. The lateral portion 120 may cover the sides of the patient. Similarly, the anterior portion 110 is oriented, when worn, to generally reside or is substantially in parallel with a frontal plane of the patient. The anterior portion 110 may be in contact with the abdominal region of the patient's spine.

Each arm (e.g., arm 100) may include a coupling section 112, as shown in FIG. 1. Each coupling section 112 is configured to removably attach/couple to the other coupling section. Regardless of the size and shape, the coupling section of the arms are so formed that complement each other and, when attached/coupled together, form a uniformly closed brace which circumferentially surrounds the body of the patient. Therefore, in some embodiments, the anterior portions 110 of the two arms of the brace (not shown) may be removably coupled together by using a hook and loop coupling. As a non-limiting example, the coupling section 112 may include a VELCRO® strip or another type of hook fastener while the coupling section for the other arm could include a loop fastener. In some embodiments, the anterior portion 110 may further include a slot. In such embodiments, an additional band may be provided in one arm which can be inserted into the slot of the other arm to couple the anterior portions of the arms.

As shown, the lumbar region of a wearer features a first band 126, an upper band 122, and a lower band 124. The first band 126 is disposed between the upper band 122 and the lower band 124. The arm 100 with slidable, internal lateral panel may feature a panel 128 which is disposed at a lateral side of the wearer and coupled to the first band 126. The panel 128 may be slidably disposed at a lateral side of the wearer and coupled to the first band 126. The first band 126 has a horizontally extending channel 132, within which the panel 128 moves. The brace with slidable, internal lateral panel 100 may feature a loop connector 140 coupled to the panel 128. Two ends of the loop connector 140 may be connected, i.e., coupled, to the panel 128, which may assist in imposing restrictions on lateral movement of the panel 128. The first end 140*a* of the loop connector 140 may be connected to the panel 128 on a first end of the panel 128 which is substantially close to a first end of the channel 132, and a second end 140*b* of the loop connector 140 may be connected to the panel 128 which is substantially close to a second end of the channel 132.

In various embodiments of the present disclosure, the panel 128 is configured to provide lateral support for the wearer. Thus, the panel 128 features a rigid material to provide such support. The loop connector 140 may be tethered to the panel 128. Moving the connector loop 140 causes moving the panel 128 laterally, which adjusts a location of the panel 128 around the lumbar region of the wearer, which in turn provides lateral support for the medial region, i.e., sides, of the wearer. As a non-limiting example, the location of the panel may be adjusted based on the size of the wearer of the brace. In some embodiments, while a first position of the panel is desirable, e.g., comfortable, for a first wearer, that position is undesirable, e.g., uncomfortable, for another wearer who is larger in size compared to the first wearer, and vice versa.

The panel 128 may include a rigid material. As a non-limiting example, the panel 128 may include a polymer with suitable stiffness to be used as the panel 128. The loop connector 140 may be tethered to the panel 128, such as D-ring style or other types of connection apertures formed in the polymer. Moving the loop connector 140 causes moving the panel 128 laterally, which adjusts a location of the panel with slidable, internal lateral panel 100 around the lumbar region of the wearer. In some embodiments, the loop connector 140 and the panel 128 may form a closed loop.

The first band 126 of the brace with slidable, internal lateral panel 100 may have a channel 132. The channel 132 is horizontally extending from the first side of the first band 126 (closer to the first side of the channel, 132*a*) to the second side of the first band 126 (closer to the second side of the channel 132*b*). The panel 128 is configured to move, i.e., slide, within the first band 126 and along the channel 132. Thus, the length of the channel 132 may determine the overall change in the location of the panel within the slidable, internal lateral panel 100. In some embodiments, the channel 132 may be used for cord/tube management. As a non-limiting example, one or more tubes, cords, cables or wires may be inserted into the channel 132. For example, wires or cords connected to medical equipment to monitor patient's vitals and/or tubes, e.g., catheters, can be inserted into the channel for wire/tube management.

The wearer of the brace may pull the loop connector 140 from the first end 132*a* to the second end 132*b* of the channel 132 to change, i.e., adjust, the location of the panel 128. In other words, moving, i.e., sliding, the panel 128 by pulling the loop connector 140 from the first end 132*a* to the second end 132*b* causes adjustment of the location of the panel 128 around the lumbar region of the wearer.

Figure 2:
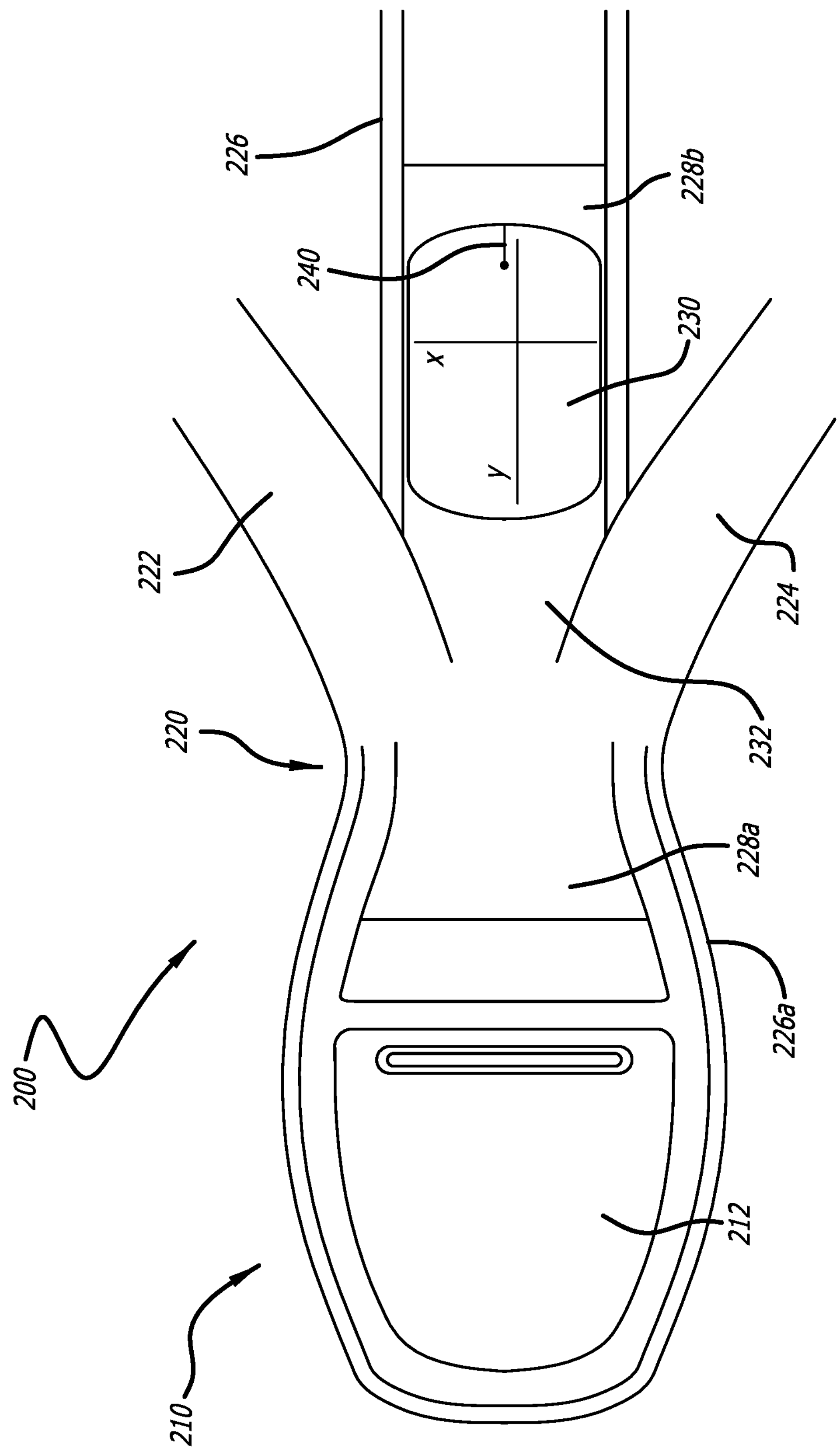
FIG. 2 is a perspective outside view of a second exemplary embodiment of the brace with slidable, internal lateral panel of FIG. 1.

Referring to FIG. 2, a perspective side view of a second exemplary embodiment of an arm 200 with one or more slidable, internal lateral panels of FIG. 1 is shown. As shown, the arm 200 with a slidable, internal lateral panel 230 may feature a first band 226, and a panel 230 slidably disposed within a channel 232 on the first band 226. A lateral movement of the panel 230 in the channel 232 may be constrained by a first boundary 228*a* disposed on a first end of the channel, and a second boundary 228*b* disposed on a second end of the channel 232. In some embodiments, the first and second boundaries 228*a* and 228*b* are formed by sewing the first band 226. In some embodiments, the first and second boundaries 228*a* and 228 are disposed within the channel 232. The size of the panel 230 is so selected that the panel 230 can only laterally slide within the channel 232. To that end, regardless of the lateral dimension of the panel 230, i.e., "y" direction, the vertical dimension of the panel 230, i.e., "x" direction, is so selected that the panel's movement is constrained in only one direction, i.e., lateral y-direction.

In some embodiments, the arm 200 with slidable, internal lateral panel may feature a handle member 240 disposed on the panel 230. The handle member 240 may be a tube knitted to the panel, a leash or any other suitable handle. The arm 200, being a portion of the lumbar brace (not shown), may further feature an upper band 222 and a lower band 224, which the first band 226 may be disposed between the upper band 222 and the lower band 224. In such embodiments, the lateral movement of the panel 230 between the first boundary 228*a* and the second boundary 228*b* adjusts the location of the panel 230 around the lumbar region of the wearer.

In some embodiments, moving the handle member 240 may cause the panel 230 to move horizontally within the channel 232. The handle member 240 may be a tube knitted to the panel 230. Additionally, or in the alternative, the handle member 240 may be a leash attached to the panel 230. It should be noted that, the handle member 240 may be any kind of suitable attachment.

Referring back to FIG. 1 now, the arm 100 with slidable, internal lateral panel 128 further features the first band 126 disposed between an upper band 124 and a lower band 122. The first band 126, the upper band 124 and the lower band 122 are attached/coupled in one end (e.g., at the posterior portion of the brace with slidable, internal lateral panel 100). The first band 126, the upper band 124 and the lower band 122 may operate independent of each other. Each of the upper band 124, the lower band 122 and the first band 126 are made of flexible materials that can flex and/or bend around the circumference body of the patient. When worn, at least portions of the upper band 124, the first babe 126 and the lower band 124 may be in contact with each other. In various embodiments, each band is made of different materials. For example, the upper and lower bands are made of a same material which is substantially softer than the material which the middle band is made of. Alternatively, at least two of the bands are made of the same materials. In some embodiments, each band is made of a different material.

Figure 3:
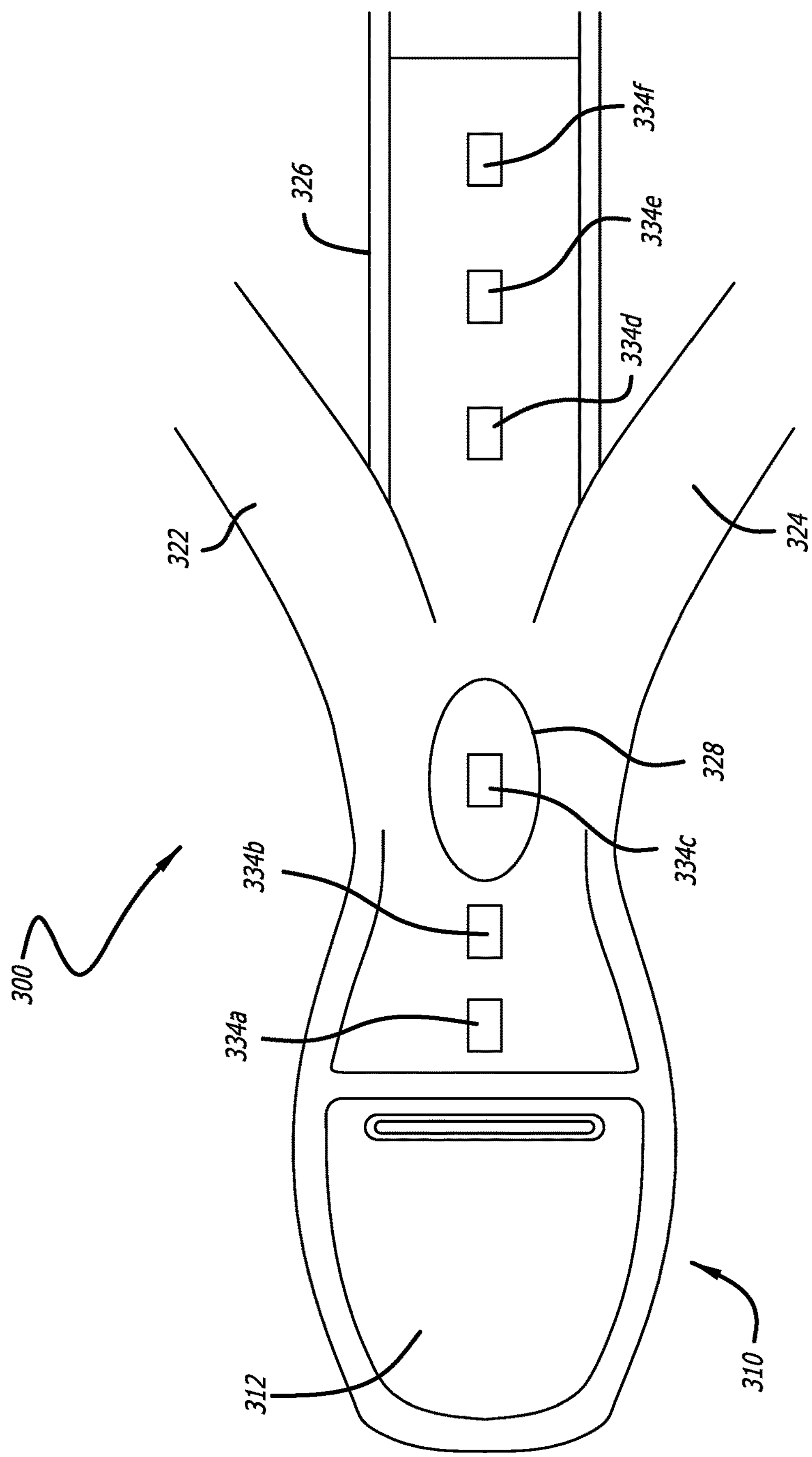
FIG. 3 is a perspective outside view of a third exemplary embodiment of the brace with slidable, internal lateral panel of FIG. 1.

Referring to FIG. 3, a perspective outside view of a third exemplary embodiment of an arm 300, being a portion of the brace, with one or more slidable, internal lateral panels of FIG. 1 is shown. As shown, the arm 300 with a slidable, internal lateral panel 328 may feature a plurality of openings 334*a*, 334*b*, 334*c*, 334*d*, 334*e*, 334*f* disposed on the first band 326. In such embodiments, the panel 328 may laterally slide between the plurality of openings 334*a*, 334*b*, 334*c*, 334*d*, 334*e*, 334*f* The first band 326 may include the horizontally extending channel, which may extend along the entire length of the first band.

The plurality of openings 334*a*, 334*b*, 334*c*, 334*d*, 334*e*, 334*f* are disposed along the channel (which is similar to the channel 132 in FIG. 1, but is not shown for the sake of simplicity) and the panel 328 slides within the channel and between the plurality of openings 334*a*, 334*b*, 334*c*, 334*d*, 334*e*, 334*f*. The first band 326 is disposed between the upper band 322 and the lower band 324. According to some embodiments, sliding the panel 328 between the plurality of openings 334*a*, 334*b*, 334*c*, 334*d*, 334*e*, 334*f* adjusts the location of the panel 328 around the lumbar region of the wearer. For example, the wearer, i.e., the patient, can adjust the location of the panel to properly fit the brace by moving the panel towards any of the openings 334*a*, 334*b*, 334*c*, 334*d*, 334*e* and 334*f*.

As an optional feature, the panel 1328 may include one or more areas along a top surface of the panel 1328 that include tactile material. This tactile material would allow for better gripping of a finger of the wearer to adjust the lateral positioning of the panel 1328 around the lumbar region.

In the foregoing description, the invention is described with reference to specific exemplary embodiments thereof. For example, the telescopic lateral panels and adjustable belt member combination, operating with a pulley subsystem, may be deployed within a LSO orthopedic brace with an architecture different than the orthopedic brace described above. Hence, it will be evident that certain components may be deployed within different types of orthopedic braces and various modifications and changes may be made thereto without departing from the broader spirit and scope of the invention as set forth in the appended claims.

What is claimed is:

1. A brace configured to wrap around a lumbar region of a wearer, comprising:

a first arm configured to wrap around a first side of the wearer; and a second arm configured to wrap around a second side of the wearer, wherein at least the first arm comprises:

a first band including a horizontally extending channel having a length extending lengthwise along the first arm, a planar panel configured to be slidably disposed within the horizontally extending channel, wherein the planar panel is configured for movement in the lengthwise direction along the horizontally extended channel located at a lateral side of the wearer when the brace is worn, and a loop connector coupled to the panel.

2. The brace of claim 1, wherein the planar panel comprises an elongated, rigid material.

3. The brace of claim 1, wherein the loop connector is tethered to the planar panel.

4. The brace of claim 1, wherein moving the loop connector causes moving the planar panel laterally and adjusting a location of the planar panel around the lumbar region of the wearer.

5. The brace of claim 1, wherein the loop connector and the planar panel form a closed loop.

6. The brace of claim 1, wherein the first band is disposed between an upper band and a lower band.

7. A brace configured to wrap around a lumbar region of a wearer, comprising:

a first band including a horizontally extending channel having a length extending lengthwise along the first band; and a planar panel configured to be slidably disposed within the horizontally extending channel, wherein the planar panel is configured for movement in the lengthwise direction along the horizontally extending channel constrained by a first and a second boundary at a first and a second end of the channel, respectively.

8. The brace of claim 7, further comprising:

a handle member disposed on the planar panel.

9. The brace of claim 8, wherein the handle member is a knitted tube.

10. The brace of claim 8, wherein the handle member is a leash.

11. The brace of claim 7, wherein the first band is disposed between an upper band and a lower band.

12. The brace of claim 7, wherein the planar panel comprises a rigid material with an elongated shape.

13. The brace of claim 7, wherein by the lateral movement of the planar panel the wearer adjusts a location of the planar panel around the lumbar region of the wearer.

14. A brace configured to wrap around a lumbar region of a wearer, comprising:

a first band having a horizontally extending channel having a length extending lengthwise along the first band;

a planar panel configured to be slidably disposed within the horizontally extending channel, wherein the planar panel is configured for movement in the lengthwise direction along the horizontally extended channel located at a lateral side of the wearer when the brace is worn; and a plurality of openings disposed on the first band.

15. The brace of claim 14, wherein the planar panel is laterally slidable between the plurality of openings.

16. The brace of claim 14, further comprising:

a second band and a third band disposed on an upper side and lower side of the first band, respectively.

17. The brace of claim 14, wherein the planar panel comprises a rigid material with an elongated shape contained within the horizontally extending channel.

18. The brace of claim 14, wherein sliding the planar panel, contained within the horizontally extending channel, between the plurality of openings adjusts a location of the planar panel around the lumbar region of the wearer.

19. The brace of claim 1, wherein the planar panel is contained within the horizontally extending channel.

20. The brace of claim 7, wherein the planar panel is contained within the horizontally extending channel.

* * * * *